US00PP20429P3

(12) United States Plant Patent
Delabroye

(10) Patent No.: US PP20,429 P3
(45) Date of Patent: Oct. 20, 2009

(54) ***HEUCHERA* PLANT NAMED 'TIRAMISU'**

(50) Latin Name: ***Heuchera* hybrid**
Varietal Denomination: Tiramisu

(76) Inventor: Sandrine Delabroye, Rue Roger Salengro 40, Hantay (FR) F-59496

( * ) Notice: Subject to any disclaimer, the term of this patent is extended or adjusted under 35 U.S.C. 154(b) by 14 days.

(21) Appl. No.: 12/002,921

(22) Filed: Dec. 19, 2007

(65) Prior Publication Data

US 2009/0165182 P1 Jun. 25, 2009

(51) Int. Cl.
*A01H 5/00* (2006.01)

(52) U.S. Cl. ..... Plt./440

(58) Field of Classification Search ..... Plt./440
See application file for complete search history.

*Primary Examiner*—June Hwu
(74) *Attorney, Agent, or Firm*—Penny J. Aguirre

(57) ABSTRACT

A new cultivar of *Heuchera* of hybrid origin, 'Tiramisu', characterized by its flat, orbicular-shaped leaves with unique coloration that changes throughout the growing season and with the temperature of the growing conditions. In the spring, the leaves are yellow-green to yellow and moderately mottled with red. In the summer, the leaves become greener with a silvery overlay. In the fall with cool temperatures, new leaves emerge that are yellow-green and heavily mottled with red with yellow-green margins and veins. 'Tiramisu' is further characterized by its compact and mounded plant habit and its cold hardiness in U.S.D.A Zone 3.

3 Drawing Sheets

Botanical classification: *Heuchera* hybrid.
Cultivar designation: 'Tiramisu'.

CROSS REFERENCE TO A RELATED APPLICATION

This application is co-pending with U.S. Plant Patent applications filed for sibling plants derived from the same cross in the inventor's breeding program that are entitled *Heuchera* Plant Named 'Beaujolais' (U.S. Plant Pat. No. 19,577), *Heuchera* Plant Named 'Encore' (U.S. Plant Pat. No. 19,578), *Heuchera* Plant Named 'Pinot Gris' (U.S. Plant Pat. No. 19,592), *Heuchera* Plant Named 'Pinot Noir' (U.S. Plant patent application Ser. No. 12/002,889) and *Heuchera* Plant Named 'Pistache' (U.S. Plant Pat. No. 19,585).

BACKGROUND OF THE INVENTION

The present invention relates to a new and distinct cultivar of hybrid *Heuchera*, botanically known as a *Heuchera* of hybrid origin and is hereinafter referred to by the cultivar name 'Tiramisu'.

The new cultivar was derived from a controlled breeding program by the inventor in Hantay, France. The inventor made a cross in summer of 2005 between *Heuchera* 'Gloire d'Orleans' (not patented, syn. *Heuchera*×*brizoides* 'Gloire d'Orleans') and *Heuchera*×*villosa* 'Caramel' (U.S. Plant Pat. No. 16,560). The goal of the breeding program was to obtain unique cultivars of *Heuchera* that combined the flowering habit of 'Gloire d'Orleans' with the vigor and unique foliage coloration of *Heuchera*×*villosa*. The inventor selected 'Tiramisu' in 2006 as a single unique plant amongst the seedlings that resulted from the above cross.

Asexual reproduction of the new cultivar was first accomplished under direction of the inventor by in vitro propagation in Rijswijk, The Netherlands in winter of 2007. Asexual reproduction of the new cultivar by division and tissue culture has shown that the unique features are stable and reproduced true to type in successive generations.

SUMMARY OF THE INVENTION

The following traits have been repeatedly observed and represent the characteristics of the new cultivar. These attributes in combination distinguish 'Tiramisu' as a new and unique cultivar of *Heuchera*.

1. 'Tiramisu' exhibits uniquely colored foliage with leaves that changes coloration throughout the season and with the temperature of the growing conditions. In the spring, the leaves are yellow-green to yellow and moderately mottled with red. In the summer, the leaves become greener with a silvery overlay. In the fall with cool temperatures, new leaves emerge that are yellow-green and heavily mottled with red with yellow-green margins and veins.
2. 'Tiramisu' exhibits large, flat, orbicular shaped leaves.
3. 'Tiramisu' exhibits a mounded and compact plant habit.
4. 'Tiramisu' is cold hardy in U.S.D.A. Zone 3.

'Tiramisu' is a unique *Heuchera* with foliage coloration that is unknown to exist in other cultivars of *Heuchera* known to the inventor. 'Tiramisu' differs from its parent plants in that 'Caramel' is a ×*villosa* hybrid and has foliage that is more orange in color and lacks red mottling and 'Gloire d'Orleans' is a ×*brizoides* hybrid with green foliage.

'Tiramisu' can be compared to *Heuchera*×*villosa* 'Citronelle' (U.S. Plant Pat. No. 17,934) for its similar leaf form and color in summer, however 'Citronelle' leaves lack red mottling. The closest comparison plants in overall leaf shape, habit, and performance are its sibling cultivars that differ in foliage coloration; 'Beaujolais' has burgundy-red leaves overlaid with silver, 'Encore' has rose-purple leaves, 'Pinot Gris' has leaves that emerge orange-yellow and mature to a rose color with a silvery overlay, 'Pinot Noir' has dark purple-gray leaves with a silver overlay, and 'Pistache' has yellow-green leaves.

BRIEF DESCRIPTION OF THE DRAWING

The accompanying colored photographs illustrate the overall appearance and distinct characteristics of the new *Heuchera*. The photographs were taken of plants grown outdoors in a trial garden in The Netherlands.

The photograph in FIG. 1 was taken in May of a plant 4 months in age and provides a view of the leaf form and coloration that is typical in spring.

Figure 1:
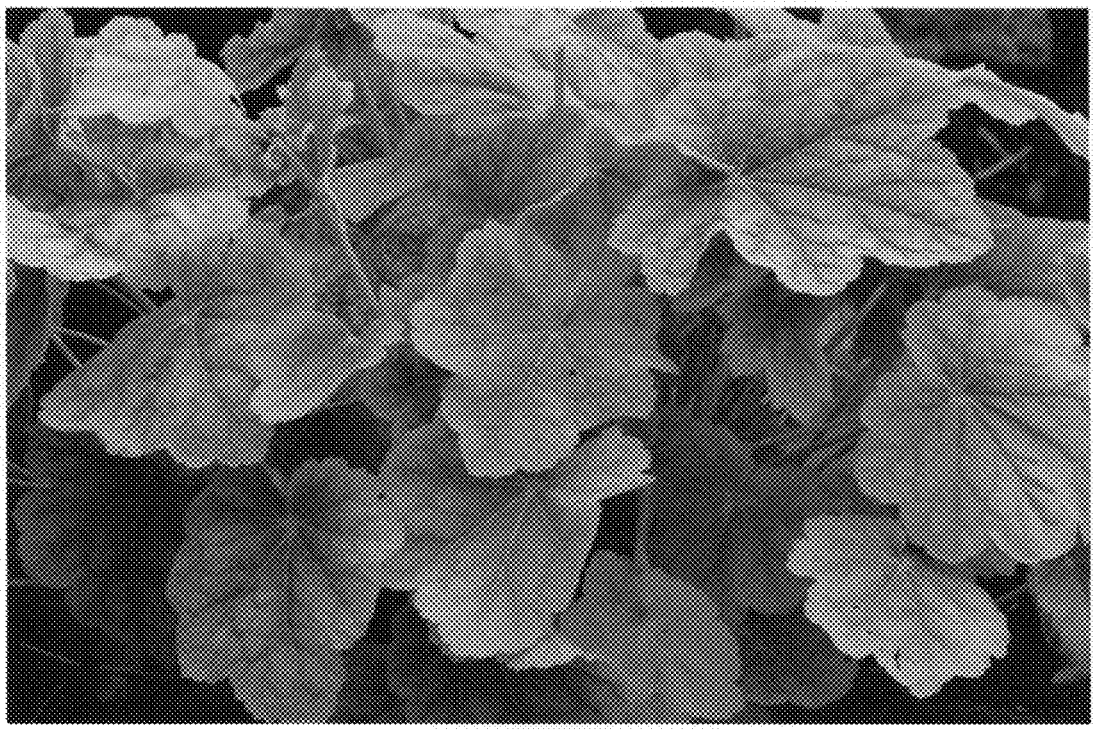
Figure 2:
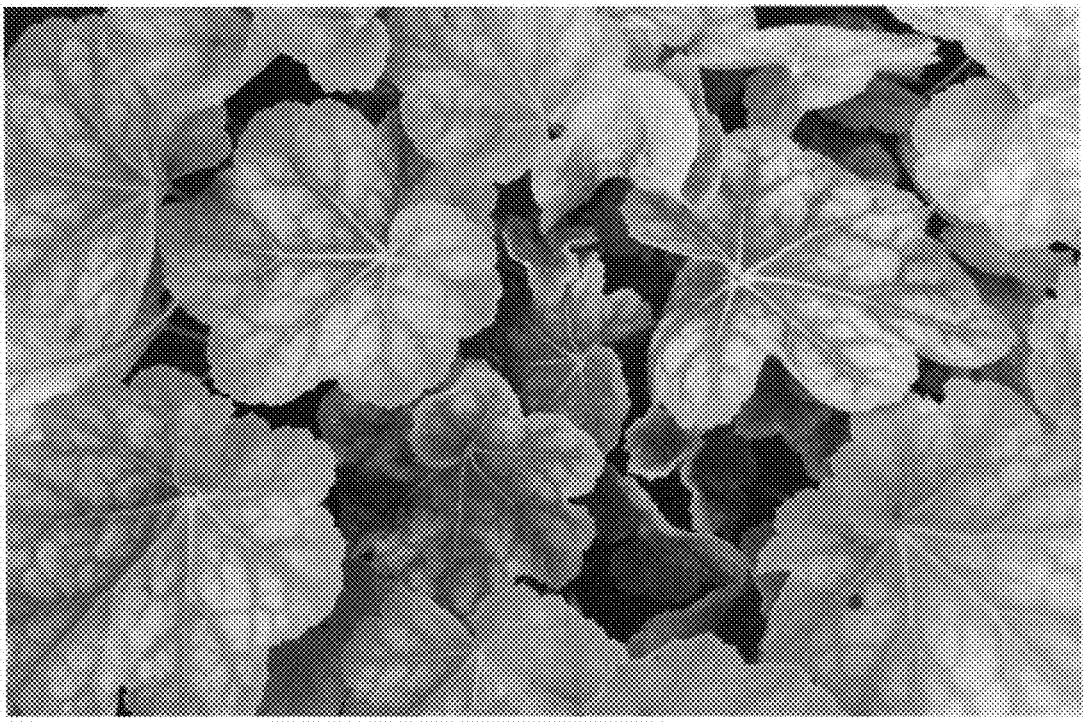

The photograph in FIG. 2 was taken in August of a plant six months in age and provides a view of the summer foliage of 'Tiramisu' on the perimeter of the plant with new growth in the center of the plant that is emerging in fall coloration due to cool night temperatures.

Figure 3:
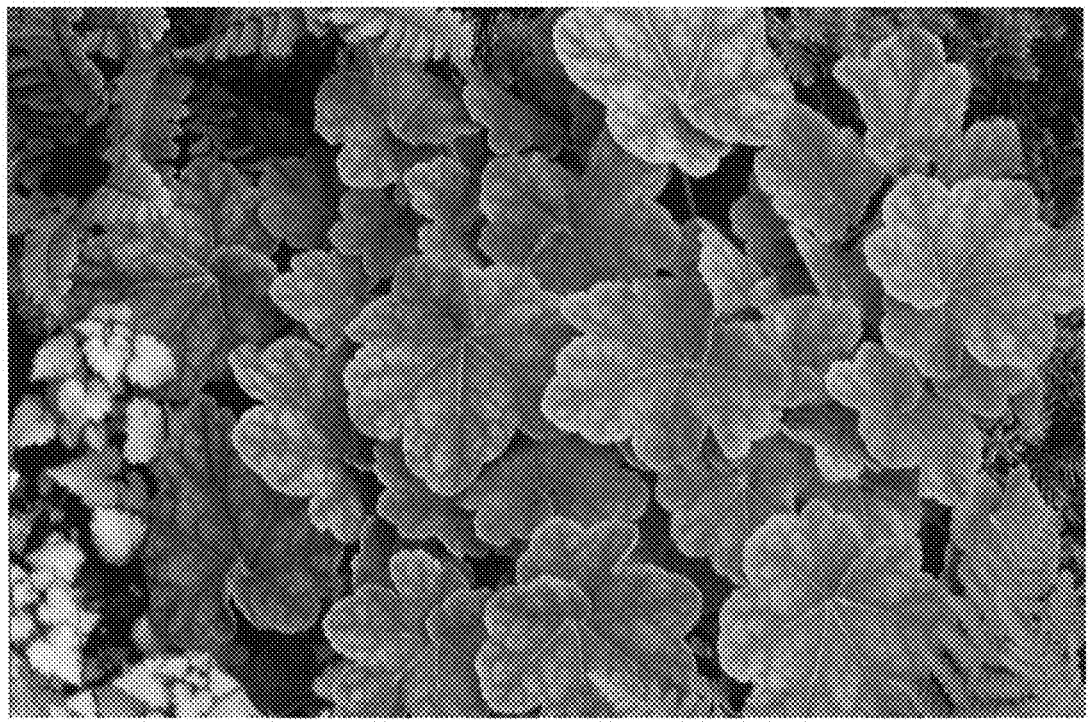

The photograph in FIG. 3 was taken in September of a plant nine months in age and provides a view of the fall foliage of 'Tiramisu'.

Figure 4:
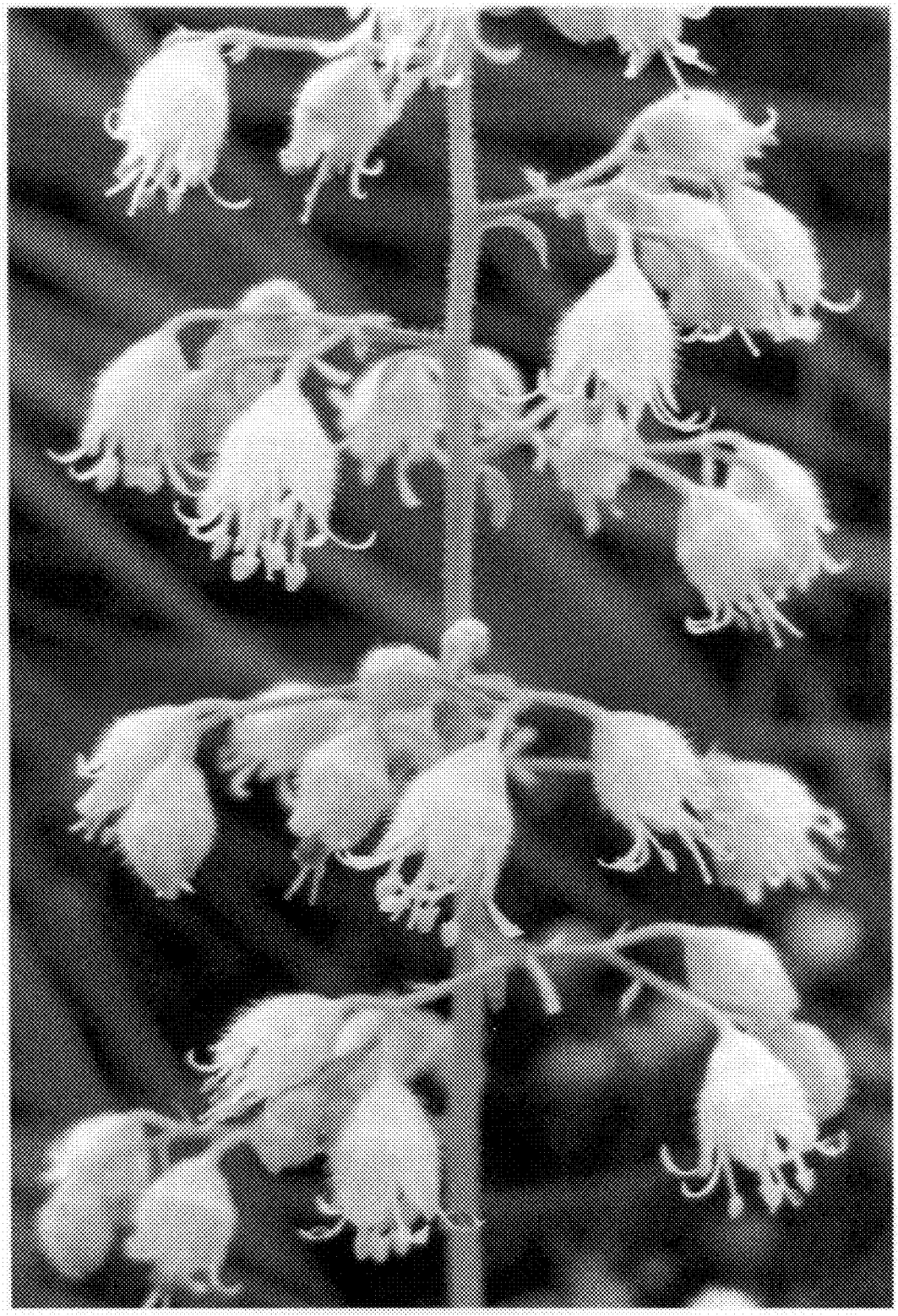

The photograph in FIG. 4 provides a close-up view of an inflorescence of 'Tiramisu'.

The colors in the photographs are as close as possible with the photographic and printing technology utilized. The color values cited in the detailed botanical description accurately describe the colors of the new *Heuchera*.

DETAILED BOTANICAL DESCRIPTION OF THE PLANT

The following is a detailed description of a 4 to 9 month-old plants of the new cultivar as grown in 2-liter containers outdoors in The Netherlands with the flower data collected from plants two years in age as grown in a 2-gallon in Hantay, France. The plants were grown under average day temperatures of 12° to 39° C. and average night temperatures of 5 to 16° C. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Blooming period.*—About 4 weeks in late summer.

*Plant habit.*—Compact, clump-forming herbaceous perennial, mounded foliage.

*Height and spread.*—Reaches about a height of about 15.4 cm in height and about 20.3 cm in width in a 2-liter container.

*Cold hardiness.*—U.S.D.A. Zone 3.

*Culture.*—Full sun to medium shade in moist, well-drained, fertile soils.

*Diseases and pests.*—Disease free in the conditions tested, no susceptibility or resistance to pests has been observed.

*Root description.*—Fibrous roots on woody rootstalks.

*Branching habit.*—Basal rosettes of leaves on petioles.

*Propagation.*—In vitro propagation is the preferred method, division are also possible.

*Root initiation.*—Roots appear in rooting media in 10 days at 20° C. in the laboratory without supplemental lighting.

*Root development.*—Rooted transplants from tissue culture fully develop at least a 9 cm container in about 20 weeks in a greenhouse with average temperatures of about 20° C. without supplemental lighting in The Netherlands.

*Growth rate.*—Moderate.

Foliage description:

*Leaf shape.*—Orbicular.

*Leaf division.*—Simple.

*Leaf base.*—Hastate, only slightly overlapping.

*Leaf apex.*—Rounded with a very small (0.7 mm) abruptly acute tip.

*Leaf venation.*—Laciniate.

*Leaf margins.*—Lobed with average of 5 lobes per leaf, lobe margins crenate.

*Leaf attachment.*—Petiolate.

*Leaf arrangement.*—Basal rosettes.

*Leaf orientation.*—Held horizontal to petiole, held nearly flat (not ruffled or curled).

*Leaf surface.*—Pubescent on upper and lower surface and rough to touch; upper surface is very sparsely covered with hairs about 0.5 mm in length and 155C in color, lower surface and margin are moderately covered with short hairs about 0.7 mm in length and 155C in color.

*Leaf color.*—Upper surface, spring; 150A to 150C changing to 8B to 8C with moderate mottling most prevalent at leaf center of 174A to 174B and veins 154D, lower surface, spring; 150A changing to 10B with diffused mottling most prevalent at leaf center of 172B to 172C and veins 154D, upper surface, summer; changes to 138B to 138C with overlay of 190D to 155C and veins 145D, lower surface, summer; changes to 145C with veins 145D, upper surface, fall; 154A to 154D with heavy mottling of 186A to 186B with conspicuous veins and margins 154A to 154D, lower surface, fall; 154A to 154D with moderate mottling of 186A to 186B with margins 154A to 154D and veins 154D.

*Leaf size.*—Average of 8.9 cm in length and 8.7 cm in width.

*Leaf quantity.*—Average of 45 per 2-liter container.

*Petioles.*—Round in shape, average length of 11.5 cm; average diameter of 3 mm, 145A to 145B in color with base tinged 182B, surface is glabrous.

*Stipules.*—None.

Flower description:

*Inflorescence type.*—Numerous small bell-shaped flowers arranged on pyramidal panicles on flower scapes emerging from the base of the rosette, each peduncle has an average of 2 pairs of lateral flowers and 2 terminal flowers.

*Inflorescence size.*—An average of 19 cm in height and about 3.5 cm in width in full bloom.

*Inflorescence number.*—An average of 12 per 2-gallon container.

*Flower fragrance.*—None detected.

*Flower quantity.*—Average of 46 flowers per flowering stem.

*Flower lastingness.*—Average of 4 days per flower, individual panicles blooms for about 3 weeks, flowers persistent.

*Flower buds.*—Broadly elliptic in shape, an average of 2.5 mm in diameter and 3.7 mm in depth, 145C in color with apex 145D, villose surface.

*Flower aspect.*—Drooping to slightly outward on peduncles held nearly horizontal to rachis.

*Flower type.*—Campanulate.

*Flower size.*—About 3.5 mm in diameter and 5.5 mm in depth.

*Petals.*—About 5, rotate arrangement and implanted in hypanthium at base, narrowly elliptic in shape, margin is entire, apex is narrowly apiculate, upper and lower surface is villose, color of upper and lower surface when opening and mature is 155B and lightly flushed with 185D, about 4.2 mm in length and 0.5 mm in width.

*Calyx.*—Campanulate, sepals fused to hypanthium, 1.5 mm in depth and 3 mm in diameter.

*Sepals.*—5, un-fused portion is elliptic in shape, about 1.5 mm in length and 0.5 mm in width, margin is entire, apex is acute, base is fused, surface villose, upper and lower surface is 145D to 150C in color.

*Bracts.*—About 3, 1 per peduncle and 0 to 2 per petiole, lanceolate in shape with 2 lateral and one terminal foliaceous appendages, 145B to 145C in color, about 6 mm in length and 1.5 mm in width, acute-leafy apex, base truncate and fused to rachis.

*Peduncles.*—Average of 2.5 cm in length and an average of 0.7 mm in width, held nearly horizontal to rachis, color 160A and suffused with 185C to 185D, surface is densely villose.

*Pedicels.*—Average of 4 mm in length and 0.5 mm in width, color 160A and suffused with 185C to 185D, villose surface, terminal is straight from peduncle and laterals are held at about a 45° angle.

*Rachis (flower scape).*—Average of 42 cm in length and an average of 2.5 mm in width, 160A in color and flushed in some regions with 185D, surface is villose, peduncle internode length is an average of 1.3 cm.

Reproductive organs:

*Gynoecium.*—2 Pistils, club-shaped, stigmas minute and 155B in color, styles are about 5.5 mm in length and 155B in color, ovaries are superior and 145D in color.

*Androcoecium.*—About 5 stamens, anthers are ovate in shape, basifixed, about 0.5 mm in diameter and 155C in color with a flush of 158D, filaments are about 5 mm in length and 155C in color, no pollen was observed.

*Seed.*—None.

It is claimed:

1. A new and distinct cultivar of *Heuchera* plant named 'Tiramisu' as herein illustrated and described.

* * * * *